United States Patent
Totake et al.

(10) Patent No.: US 8,916,841 B2
(45) Date of Patent: Dec. 23, 2014

(54) PARTICLE THERAPY SYSTEM

(71) Applicant: Hitachi, Ltd., Tokyo (JP)

(72) Inventors: Satoshi Totake, Tokai (JP); Masumi Umezawa, Mito (JP); Tomohisa Imagawa, Tokai (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 13/857,573

(22) Filed: Apr. 5, 2013

(65) Prior Publication Data
US 2013/0267756 A1    Oct. 10, 2013

(30) Foreign Application Priority Data

Apr. 10, 2012   (JP) .................................. 2012-089578

(51) Int. Cl.
   *G21K 5/04* (2006.01)
   *A61N 5/10* (2006.01)

(52) U.S. Cl.
   CPC ............. *A61N 5/1048* (2013.01); *A61N 5/1077* (2013.01); *A61N 5/1049* (2013.01); *A61N 5/1043* (2013.01); *A61N 2005/1087* (2013.01); *A61N 5/103* (2013.01)
   USPC ................. 250/492.3; 250/492.1; 250/396 R; 250/397; 600/1; 315/500

(58) Field of Classification Search
   USPC ............... 250/396 R, 397, 423 R, 424, 492.1, 250/492.2; 600/1; 315/500, 501, 502, 503, 315/504, 505
   See application file for complete search history.

(56) References Cited

U.S. PATENT DOCUMENTS

| | | | |
|---|---|---|---|
| 2009/0283702 A1* | 11/2009 | Umezawa et al. | ......... 250/492.3 |
| 2011/0147604 A1 | 6/2011 | Iwata | |
| 2011/0240875 A1 | 10/2011 | Iwata | |
| 2011/0260074 A1 | 10/2011 | Honda et al. | |

FOREIGN PATENT DOCUMENTS

| | | |
|---|---|---|
| JP | 08-298200 A | 11/1996 |
| JP | 2005/296162 A | 10/2005 |

* cited by examiner

*Primary Examiner* — Nicole Ippolito
(74) *Attorney, Agent, or Firm* — Mattingly & Malur, PC

(57) ABSTRACT

A particle therapy system is capable of reducing an increase in treatment time caused by the initialization operation of magnets in the execution of the scanning irradiation method successively changing the energy level of a beam extracted from an accelerator. An irradiation control apparatus has a scheme that calculates setting vales of excitation current for bending magnets for a transport system on every irradiation condition (energy condition), and sets appropriate excitation current values according to the irradiation sequence. The irradiation control apparatus 35 prestores in a current supply control table 1 reference current values determined corresponding to energy levels of the ion beam, prestores in current supply compenzation value tables 1, 2 compenzation current values determined corresponding to energy levels of the ion beam and numbers of times of changing the energy level, and calculates the excitation current value of the magnets by using the values prestored in the tables.

4 Claims, 8 Drawing Sheets

FIG. 4

MAGNET CURRENT SUPPLY TABLE 1

| ENERGY [MeV] | REFERENCE MAGNET EXCITATION CURRENT VALUE [A] | | | |
|---|---|---|---|---|
| | BENDING MAGNET 15 | BENDING MAGNET 20A | BENDING MAGNET 20B | BENDING MAGNET 20C |
| 230 | 450 | 420 | 420 | 400 |
| 225 | 445 | 415 | 415 | 395 |
| 220 | 440 | 410 | 410 | 390 |
| 215 | 435 | 405 | 405 | 385 |
| 210 | 430 | 400 | 400 | 380 |
| 205 | 425 | 395 | 395 | 375 |
| 200 | 420 | 390 | 390 | 370 |
| . | | . | . | |
| . | | . | . | |
| . | | . | . | |
| 70 | 290 | 260 | 260 | 240 |

FIG. 5

MAGNET CURRENT SUPPLY COMPENSATION VALUE TABLE 1

| ENERGY SCAN STEP NUMBER | COMPENSATION VALUE RATIO [%] |
|---|---|
| 1 | 0 |
| 2 | 10 |
| 3 | 20 |
| 4 | 30 |
| 5 | 40 |
| 6 | 50 |
| 7 | 60 |
| . | . |
| . | . |
| . | . |
| 100 | 100 |

FIG. 6

MAGNET CURRENT SUPPLY COMPENSATION VALUE TABLE 2

| ENERGY [MeV] | BASIC COMPENSATION VALUE FOR MAGNET EXCITATION CURRENT [A] | | | |
|---|---|---|---|---|
| | BENDING MAGNET 15 | BENDING MAGNET 20A | BENDING MAGNET 20B | BENDING MAGNET 20C |
| 230 | -3.0 | -3.0 | -3.0 | -3.0 |
| 225 | -2.7 | -2.7 | -2.7 | -2.7 |
| 220 | -2.4 | -2.4 | -2.4 | -2.4 |
| 215 | -2.0 | -2.0 | -2.0 | -2.0 |
| 210 | -2.0 | -2.0 | -2.0 | -2.0 |
| 205 | -1.8 | -1.8 | -1.8 | -1.8 |
| 200 | -1.5 | -1.5 | -1.5 | -1.5 |
| . | . | . | . | . |
| . | . | . | . | . |
| . | . | . | . | . |
| 70 | -0.8 | -0.8 | -0.8 | -0.8 |

PARTICLE THERAPY SYSTEM

BACKGROUND OF THE INVENTION

1. Field of the Invention

The present invention relates to a particle therapy system for treating tumors such as cancers by irradiating the tumors with a proton beam or a heavy ion beam such as a carbon ion beam.

2. Description of the Related Art

A particle therapy, which irradiates a target volume (tumor volume) with an ion beam such as a proton beam or a carbon ion beam, is well known as one of the cancer treatment methods. When an ion beam (proton beam, carbon ion beam, etc.) with high energy enters a material, the ion beam loses much of its energy at the end of its propagation path (range). The particle therapy takes advantage of such a property of the ion beam and applies the ion beam to the patient so as to make the beam lose much of its energy in cancer cells. In the particle therapy, a dose distribution conformal to the shape of the target volume is formed by adjusting the spatial broadening (spatial distribution) and the energy of the ion beam A particle therapy system used for the particle therapy comprises an ion source for generating ions, an accelerator for accelerating the ions generated by the ion source and thereby forming an ion beam, a beam transport system for transporting the ion beam extracted from the accelerator, and an irradiation device for irradiating the target volume with the ion beam according to a desired dose distribution.

The accelerator used for the particle therapy system can be a synchrotron or a cyclotron, for example. The function of accelerating injected ions to a prescribed energy level and outputting the accelerated ions as an ion beam is common to the synchrotron and the cyclotron.

The ion beam extracted from the accelerator is transported by the beam transport system to the irradiation device. The beam transport system is equipped with bending electromagnets (hereinafter referred to as "magnet" or "magnets") for changing the propagation direction of the ion beam, steering electromagnets (hereinafter referred to as "magnet" or "magnets") for the fine adjustment of the beam propagation direction, and quadrupole electromagnets (hereinafter referred to as "magnet" or "magnets") for giving convergence/divergence effects to the ion beam. By properly adjusting the levels of excitation of these magnets, a beam in an appropriate size and at an appropriate position can be transported to the irradiation device.

There are cases where the beam transport system and the irradiation device are mounted on a rotary gantry in order to irradiate the target volume with beams from multiple directions. The beam transport system of the particle therapy system having the rotary gantry can be roughly divided into a rotary beam transport system which is mounted on the rotary gantry and a fixed beam transport system which is mounted/fixed on the building.

The irradiation device forms an ion beam irradiation field that is conformal to the shape of the target volume. The irradiation field can be formed by two types of methods: a scatterer irradiation method and a scanning irradiation method. With the technological progress, the mainstream is shifting toward the scanning irradiation method capable of high-accuracy irradiation. An irradiation device employing the scanning irradiation method is equipped with two scanning electromagnets (hereinafter referred to as "magnet" or "magnets") for scanning the beam. In order to irradiate exclusively the target volume, the beam in the irradiation device is scanned by these scanning magnets within a specified area orthogonal to the beam propagation direction. By successively changing the energy of the beam extracted from the accelerator, the reachable depth of the beam can be changed and the irradiation field conformal to the shape of the target volume can be formed.

Further, in the particle therapy, the reproducibility of the beam irradiation position is generally enhanced by performing initialization operation on the magnets to maintain the beam irradiation position accuracy at a high level.

A method for enhancing the accuracy and the reproducibility of the beam irradiation position has been described in JP-2005-296162-A. In this method, the energy level of the beam extracted from the accelerator is changed successively in order to form the irradiation field conformal to the shape of the target volume. To avoid ill effect of the hysteresis of the scanning magnets, a conversion table regarding conversion between beam position data detected by a beam position monitor and preset current values of the scanning magnets is stored in a storage device and the current values (electric current values) of the scanning magnets are set by using the stored conversion table according to beam position data determined based on treatment plan data.

JP-8-298200-A has described a method for uniformizing the remanent magnetization of the synchrotron magnets on each switching of the energy level in the operation successively changing the energy level of the ion beam. In this method, an initialization operation of temporarily increasing the excitation current value of each magnet (reexcitation) to a current value for the initialization (without shifting to the beam deceleration process immediately after the completion of the beam extraction at each energy level) and then demagnetizing each magnet is performed also on the magnets of the extraction beam transport system in the same way as the synchrotron magnets.

SUMMARY OF THE INVENTION

As mentioned above, the scanning irradiation method successively changes the energy level of the beam extracted from the accelerator in order to form the irradiation field conformal to the shape of the target volume. To carry out the treatment irradiation with high beam irradiation position accuracy in the operation successively changing the energy level, it is desirable to perform the initialization operation on the synchrotron (accelerator) magnets and the transport system magnets on each switching of the energy level.

The conventional technique of JP-2005-296162-A is a proposal of a method for avoiding the ill effect of the hysteresis of the scanning magnets when the beam is scanned in one layer, and thus is not a technique for compensating for the change in the remanent magnetization of the accelerator magnets and the transport system magnets on each switching of the energy level.

The conventional technique of JP-8-298200-A performs the initialization operation not only on the synchrotron (accelerator) magnets but also on the transport system magnets on each switching of the energy level by temporarily increasing the excitation current value of each magnet to the initialization current value (reexcitation) and then demagnetizing each magnet.

In general, each of the synchrotron magnets operates on a pattern power supply and carries out pattern operation of successively increasing and decreasing the magnetic field intensity in the order of injection, acceleration, extraction and deceleration at each energy level. On the other hand, each of the transport system magnets generally operates on a DC power supply and carries out operation of changing its excitation current value (set at a constant value corresponding to the energy level of the ion beam) stepwise on each switching of the energy level.

If the initialization operation of temporarily increasing the excitation current value to the initialization current value (reexcitation) and then dropping the excitation current value (demagnetization) is performed on the transport system magnets (operating on DC power supplies as mentioned above) on each switching of the energy level according to the idea of JP-8-298200-A, the following problem occurs: Since the responsiveness of DC power supplies is three to four times slower than that of pattern power supplies, the time necessary for the switching of the energy level increases considerably and the treatment irradiation time can be doubled depending on the conditions of the irradiation. If pattern power supplies are employed for the transport system magnets, the increase in the treatment irradiation time can be avoided differently from the case employing DC power supplies. However, this leads to an increase in the power supply cost.

It is therefore the primary object of the present invention to provide a particle therapy system capable of reducing the increase in the treatment time caused by the initialization operation of the magnets in the execution of the scanning irradiation method successively changing the energy level of the beam extracted from the accelerator.

In order to achieve the above object, a particle therapy system in accordance with the present invention comprises an irradiation control apparatus which controls the excitation current value of at least one magnet installed in the accelerator or the beam transport system so as to increase or decrease the excitation current value stepwise based on the energy level of the extracted ion beam and the number of times of stepwise changing of the energy level of the extracted ion beam. Specifically, the irradiation control apparatus prestores reference current values determined corresponding to energy levels of the charged particle beam (ion beam) and compensation current values determined corresponding to energy levels of the ion beam and numbers of times of changing the energy level, and calculates the excitation current value of the magnet by using the reference current value and the compensation current value. With this configuration, excitation current values avoiding the influence of the energy level of the ion beam and the number of times of changing the energy level can be set to magnets operating on DC power supplies (especially, bending magnets in the transport system). Consequently, treatment irradiation control with high accuracy of the beam irradiation position becomes possible without causing an increase in the treatment time or the power supply cost.

According to the present invention, it is possible to provide a particle therapy system capable of reducing the increase in the treatment time caused by the initialization operation of the magnets in the execution of the scanning irradiation method successively changing the energy level of the beam extracted from the accelerator.

BRIEF DESCRIPTION OF THE DRAWINGS

FIG. 4 shows a current supply control table which is used for magnet excitation current control.

FIG. 5 shows a current supply compensation value table which is used for the magnet excitation current control.

FIG. 6 shows another current supply compensation value table which is used for the magnet excitation current control.

DESCRIPTION OF THE PREFERRED EMBODIMENTS

Figure 1:
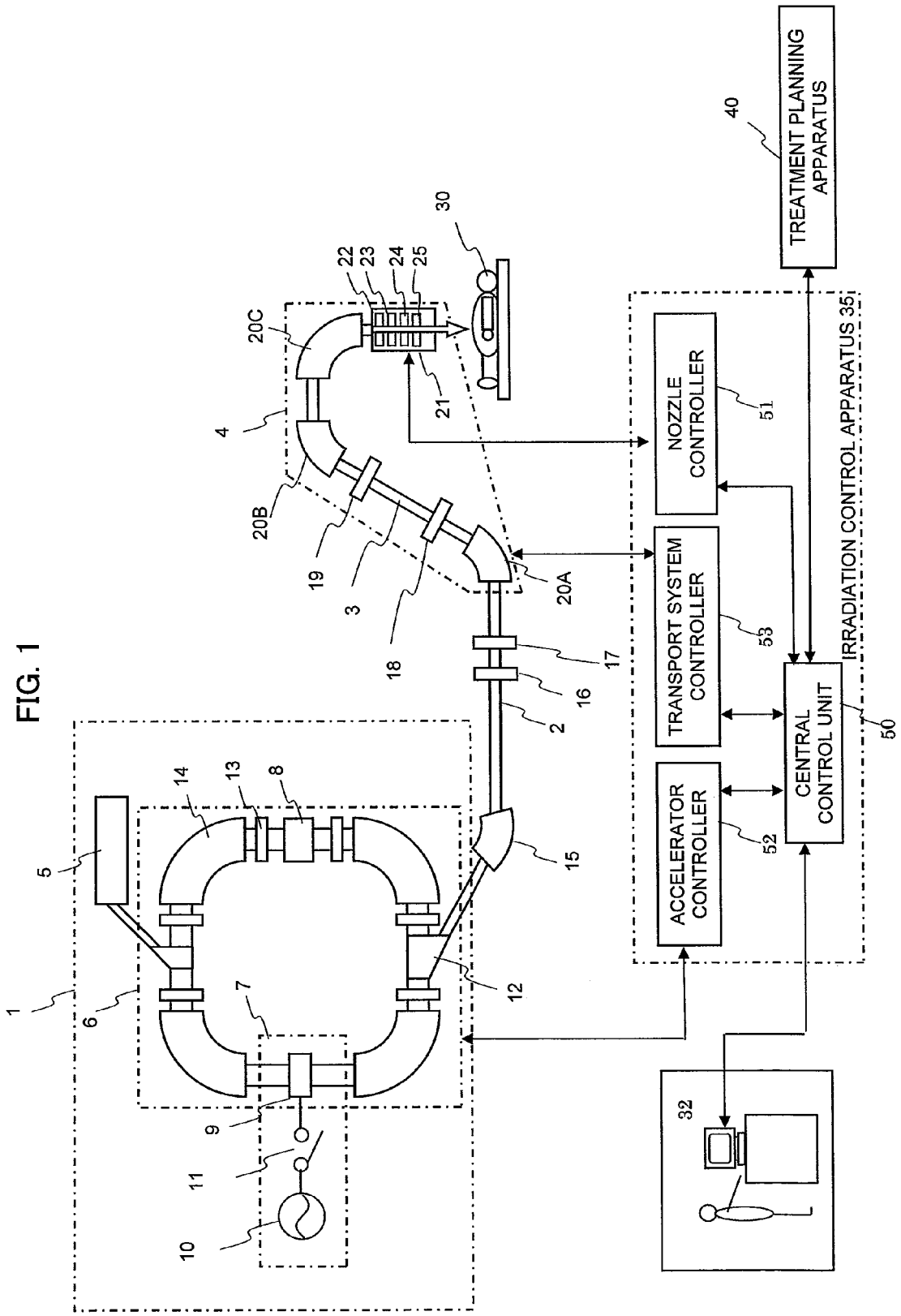
FIG. 1 is a schematic block diagram showing the overall configuration of a particle therapy system in accordance with an embodiment of the present invention.

Referring now to the drawings, a description will be given in detail of a preferred embodiment in accordance with the present invention.

FIG. 1 is a schematic block diagram showing the overall configuration of a particle therapy system in accordance with an embodiment of the present invention. In this embodiment, the particle therapy system is configured as explained below.

As shown in FIG. 1, the particle therapy system of this embodiment comprises an ion beam generating device (particle beam generating device) 1, a high-energy beam transport system 2 connected downstream of the ion beam generating device 1, and a rotary gantry 4 having a gantry beam transport system 3.

The ion beam generating device 1 includes a synchrotron 6 and a linear accelerator 5 having an ion source. The synchrotron 6 includes an extraction high-frequency power application device 7 and an acceleration high-frequency power application device 8. The extraction high-frequency power application device 7 (high-frequency power application device for the extraction of the ion beam from the synchrotron 6) is formed by connecting a high-frequency power application electrode 9 placed in the orbit of the synchrotron 6 to a high-frequency power supply 10 via an ON/OFF switch 11. The linear accelerator 5 generates an ion beam (particle beam) by accelerating ions (protons, carbon ions, etc.) generated in the ion source and injects the ion beam into the synchrotron 6. The ion beam circulates in the synchrotron 6 and is accelerated up to a preset energy level when necessary energy is given by acceleration energy generated by the acceleration high-frequency power application device 8. The energy level of the ion beam is determined to suit the depth of the target volume in the patient's body from the body surface (irradiation depth) measured in the beam irradiation direction. When necessary energy has been given to the ion beam circulating in the synchrotron 6, extraction high-frequency power (high-frequency electric power used for the extraction of the ion beam) is supplied from the high-frequency power supply 10 to the high-frequency power application electrode 9 via the closed switch 11 and is applied to the ion beam by the electrode 9. The ion beam circulating within the stability limit is shifted to the outside of the stability limit by the application of the high-frequency power, by which the ion beam is extracted from the synchrotron 6 via an extraction deflector 12. For the extraction of the ion beam, electric currents supplied to quadrupole magnets 13 and bending magnets 14 of the synchrotron 6 are kept at preset values (electric current set values) and the stability limit is also kept substantially at a constant level. The extraction of the ion beam from the synchrotron 6 is ended by stopping the application of the high-frequency power to the high-frequency power application electrode 9 by opening the switch 11.

The ion beam (hereinafter referred to simply as a "beam") extracted from the synchrotron 6 is transported downstream (toward an irradiation nozzle 21) by the high-energy beam transport system 2. The high-energy beam transport system 2 includes a bending magnet 15, quadrupole magnets 16 and steering magnets 17. The beam supplied to the high-energy beam transport system 2 is lead to the gantry beam transport system 3 via a bending magnet 15. The gantry beam transport system 3 attached to the rotary gantry 4 includes quadrupole magnets 18, steering magnets 19, and bending magnets 20A, 20B and 20C. The beam lead to the gantry beam transport system 3 is transported to the irradiation nozzle 21 (irradiation device) via these magnets. The irradiation nozzle 21, employing the scanning irradiation method, has been mounted on a rotary drum of the rotary gantry 4. A profile monitor 22, scanning magnets 23, a dose monitor 24, and a spot position monitor 25 are arranged inside the irradiation nozzle 21. The beam entering the irradiation nozzle 21 passes through the profile monitor 22 placed on the beam path, gets deflected by two scanning magnets 23, passes through the dose monitor 24 and the spot position monitor 25, and then irradiates the target volume inside the body of the patient 30.

The particle therapy system of this embodiment comprises an irradiation control apparatus 35 for controlling the irradiation of the beam. As shown in FIG. 1, the irradiation control apparatus 35 includes a central control unit 50, a nozzle controller 51, an accelerator controller 52, and a transport system controller 53. The central control unit 50 is connected to the nozzle controller 51, the accelerator controller 52 and the transport system controller 53. The central control unit 50 is connected also to a treatment planning apparatus 40 to receive treatment plan data sent from the treatment planning apparatus 40. The nozzle controller 51 controls the profile monitor 22, the scanning magnets 23, the dose monitor 24 and the spot position monitor 25. The accelerator controller 52 controls the devices constituting the synchrotron 6. The transport system controller 53 controls the devices constituting the high-energy beam transport system 2 and the gantry beam transport system 3. Further, a human interface terminal (HMI terminal) 31 is connected to the central control unit 50.

The central control unit 50 loads the aforementioned treatment plan data regarding the patient (who is going to receive the treatment) from the treatment planning apparatus 40. As mentioned above, the irradiation depth corresponds to the energy level of the beam. The energy level of the beam corresponds to the control pattern of the excitation currents supplied to the magnets of the synchrotron 6, the high-energy beam transport system 2 and the gantry beam transport system 3. Specifically, an electric power supply control table has been prestored in the central control unit 50. For example, values or patterns of excitation power to be supplied to the quadrupole magnets 13 and the bending magnets 14 of the ion beam generating device 1 including the synchrotron 6 and to the quadrupole magnets 16 and 18, the steering magnets 17 and 19 and the bending magnets 15, 20A, 20B and 20C of the beam transport systems 2 and 3 have been preset for each energy level (150 MeV, 145 MeV, 140 MeV, etc.).

Figure 2:
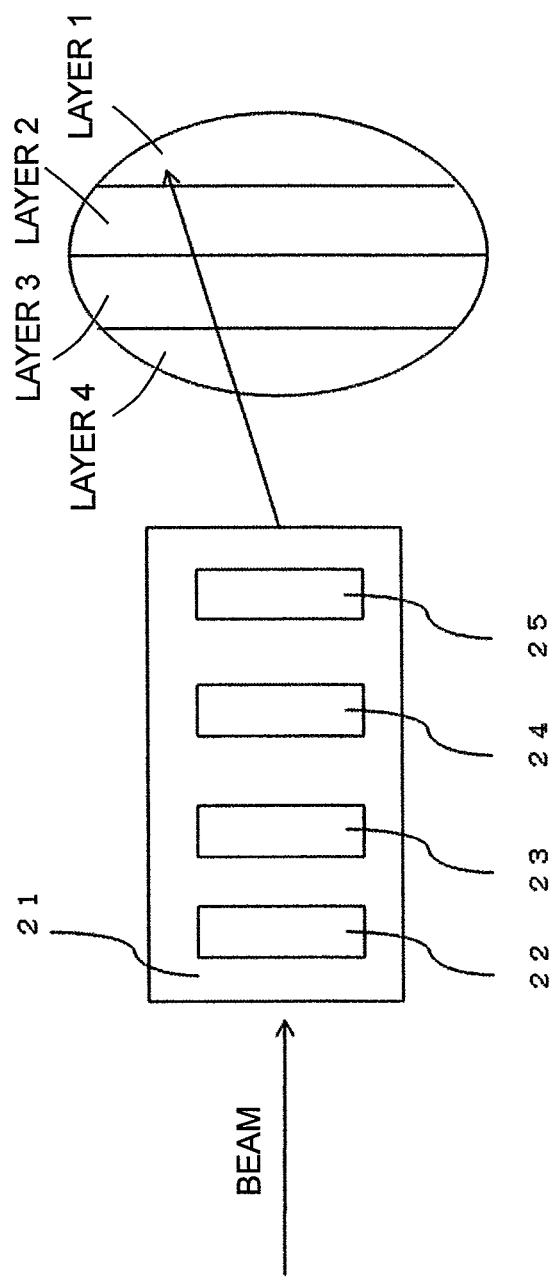
FIG. 2 is a schematic diagram for explaining the scanning irradiation method in which the target volume is segmented into layers and the target volume is irradiated with an even dose by successively irradiating each layer with a particle beam while scanning the particle beam in lateral directions with scanning magnets.

Next, the beam irradiation method employed by the particle therapy system of this embodiment will be explained referring to FIG. 2. The target volume is segmented into laminar regions (layers) as indicated with the reference characters 1, 2, 3 and 4 in FIG. 2. In this case, it is possible to irradiate each layer with a beam of a constant energy level. The layer 1 is situated at the deepest position in the beam propagation direction and the layers 2, 3 and 4 gradually get shallower in this order. Each layer is irradiated by use of the two scanning magnets 23 so that the entire layer is scanned by the beam. The central control unit 50 sends the irradiation pattern which has been set by the treatment planning apparatus 40 to the nozzle controller 51. The nozzle controller 51 controls the irradiation nozzle 21 so as to scan the beam according to the data (irradiation pattern) and irradiate each layer with the preset dose. When the irradiation of a layer is finished, the nozzle controller 51 sends an irradiation completion signal regarding the layer to the central control unit 50. The central control unit 50 receiving the irradiation completion signal sends a beam energy alteration signal to the accelerator controller 52 and the transport system controller 53. In response to the beam energy alteration signal, the accelerator controller 52 and the transport system controller 53 set a magnet excitation current set value corresponding to the next energy level to a power supply unit of each magnet, by which beam extraction preparation for the next energy level is completed. When the beam extraction preparation is completed, the central control unit 50 sends an extraction preparation completion signal to the nozzle controller 51. In response to the extraction preparation completion signal, the nozzle controller 51 starts the irradiation of the next layer. As explained above, the beam is scanned in a three-dimensional pattern by scanning the beam laterally (in the lateral directions) by using the scanning magnets and successively changing the beam energy in the depth direction. The above irradiation method is the one called "scanning irradiation method". The scanning irradiation method is an irradiation method capable of giving the dose exclusively to the target volume and preventing the irradiation of normal tissue around the target volume. Incidentally, the operation successively changing the energy (specifically, increasing/decreasing stepwise the energy level of the ion beam extracted from the accelerator) is called "energy scan operation".

Next, the operation of the irradiation control apparatus 35 for the energy scan operation, as a characteristic feature of this embodiment, will be explained below.

The central control unit 50 receives prescription data regarding the patient (who is going to receive the treatment) from the treatment planning apparatus 40. The prescription data includes information on the treatment room, the angles of the rotary gantry 4, the beam energy (energy of the irradiating beam), the beam scan ranges, the irradiation amount, etc. Based on the prescription data, the central control unit 50 generates control command data (control command information) for controlling the magnets arranged along the beam path inside the ion beam generating device 1 and the beam transport systems 2 and 3. The control command data is generated by use of tables specifying magnet excitation levels for each energy level and is outputted to the power supply units of the magnets. Among the power supply units, those of the magnets of the synchrotron 6 (hereinafter referred to as "synchrotron magnets") are implemented by using pattern power supplies having high response speeds, while those of the magnets of the high-energy beam transport system 2 and the gantry beam transport system 3 (hereinafter referred to as "transport system magnets") are implemented by using low-priced DC power supplies.

Figure 3:
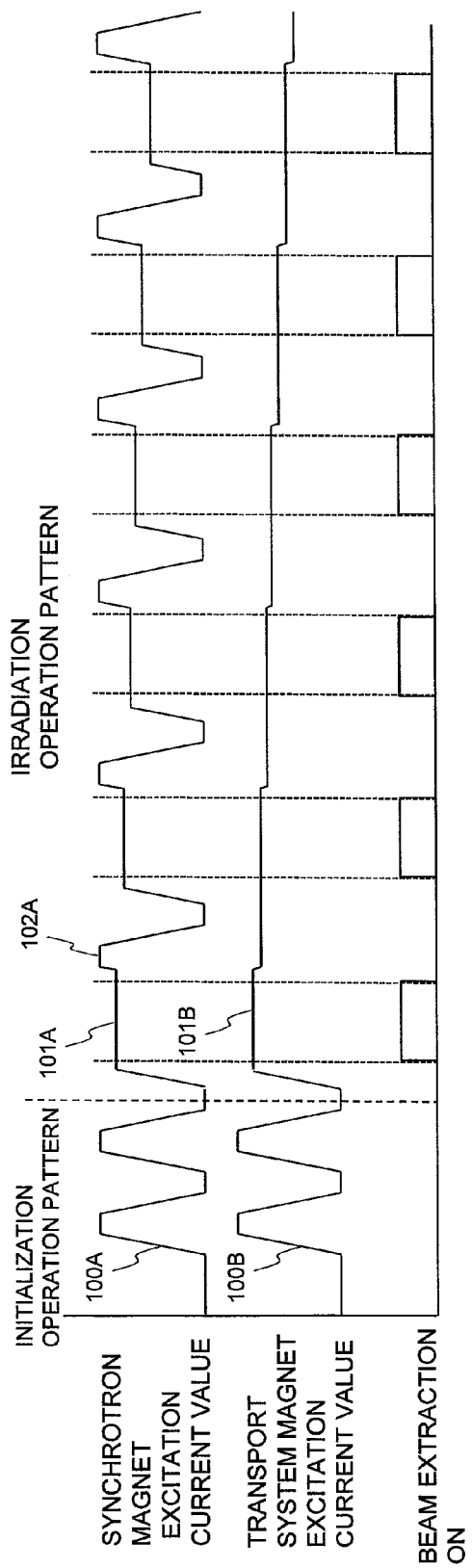
FIG. 3 is a graph showing excitation current patterns for synchrotron magnets and transport system magnets during the scan irradiation operation.

Here, the control of the excitation currents supplied to the synchrotron magnets and the transport system magnets during the energy scan operation in this embodiment will be explained. FIG. 3 is a graph showing the excitation current patterns for the synchrotron magnets and the transport system magnets during the energy scan operation in which the energy of the extracted ion beam is decreased stepwise.

In the particle therapy according to this embodiment, initialization operations of the magnets (indicated with reference characters 100A and 100B in FIG. 3) are conducted first in order to carry out the beam irradiation with high reproducibility of the beam position. The magnetization of the magnets arranged on the beam path can be uniformized by the initialization operation, by which variations in the magnetization can be suppressed and the reproducibility of the beam irradiation position can be increased. Subsequently, the synchrotron magnets (operating on the pattern power supplies) are operated in pattern operation of increasing and decreasing the magnetic field intensity as indicated with the reference character 101A in FIG. 3 even after the initialization operation. The excitation current value of each synchrotron magnet in the ion beam extraction period is controlled so that the value decreases stepwise and in stages to suit the energy of the extracted ion beam. On the other hand, each of the transport system magnets (operating on the DC power supplies) after the initialization operation is set at a fixed excitation current value to suit the energy of the extracted ion beam as indicated with the reference character 101B in FIG. 3. The excitation current value of each transport system magnet is changed stepwise corresponding to the change in the energy level. In general, the time necessary for changing the energy level is approximately 1-10 seconds (corresponding to one operation cycle of the synchrotron) although the time varies depending on the conditions of the irradiation.

Further, in the energy scan operation according to this embodiment, the initialization operation is performed on the synchrotron magnets on every switching of the energy level as indicated with the reference character 102A in FIG. 3 in order to carry out the treatment irradiation with high positional accuracy. In this initialization operation 102A, the excitation current value is temporarily increased to a current value (maximum current value) for the initialization (reexcitation) without immediately shifting to the deceleration process after the completion of the beam extraction at each energy level, and then the magnets are demagnetized. Therefore, the initialization operation 102A is different from the aforementioned initialization operations 100A and 100B.

It is possible to perform the initialization operation on every switching of the energy level (temporarily increasing the excitation current value to the initialization current value (reexcitation) and then demagnetizing each magnet) also on the transport system magnets (operating on the DC power supplies) in the same way as the synchrotron magnets. However, the responsiveness of DC power supplies is three to four times slower than that of pattern power supplies and thus performing the initialization operation by using the DC power supplies considerably increases the time necessary for the switching of the energy level. As a result, the treatment irradiation time can be doubled depending on the irradiation conditions. The increase in the treatment irradiation time can of course be avoided by employing pattern power supplies also for the transport system magnets; however, this leads to an increase in the power supply cost.

In this embodiment designed in consideration of the above problems, excitation current control for making it possible to perform the treatment irradiation without the initialization operation of the transport system magnets is carried out while employing conventional DC power supplies for the transport system magnets, especially for the transport systems' bending magnets 15, 20A, 20B and 20C having the maximum effect on the positional accuracy of the beam irradiation. The outline of the excitation current control is as follows: The excitation current value of each magnet is calculated by use of a reference current value determined according to the energy (energy level) of the extracted beam and a correction value (compensation value) determined according to the number of times of the change of the energy level to reach the intended energy level. Each magnet is controlled according to the calculated excitation current value. The details of the excitation current control will be explained below.

FIG. 4 shows a current supply control table 1 (first data table) used for the magnet excitation current control of the transport systems. FIG. 5 shows a current supply compensation value table 1 (second data table) used for the magnet excitation current control. FIG. 6 shows a current supply compensation value table 2 (third data table) used for the magnet excitation current control. The magnet excitation level for each energy level (i.e., the value of the excitation current supplied to each magnet for the beam irradiation at each energy level) is calculated by using the three data tables 1, 2 and 3.

The current supply control table 1 stores reference magnet excitation current values (i.e., reference values of the excitation current supplied to each magnet). Specifically, the current supply control table 1 stores the value of the excitation current to be supplied to each magnet when the beam irradiation at a certain energy level is conducted without considering the remanent magnetization, that is, when monoenergetic operation is performed without executing the energy scan operation. This table, for registering excitation current values necessary for realizing bending magnet excitation levels capable of properly deflecting the beam during the monoenergetic operation, is determined during the beam commissioning.

The current supply compensation value tables 2 and 3 are tables used for the fine adjustment of the control command data stored in the current supply control table 1. Specifically, current set values (electric current set values) for compensating for a change in the magnetic field (remanent magnetization) due to the hysteresis caused by the energy scan operation are registered in the current supply compensation value tables 2 and 3.

The details of the current supply compensation value tables 2 and 3 will be explained below.

Figure 7:
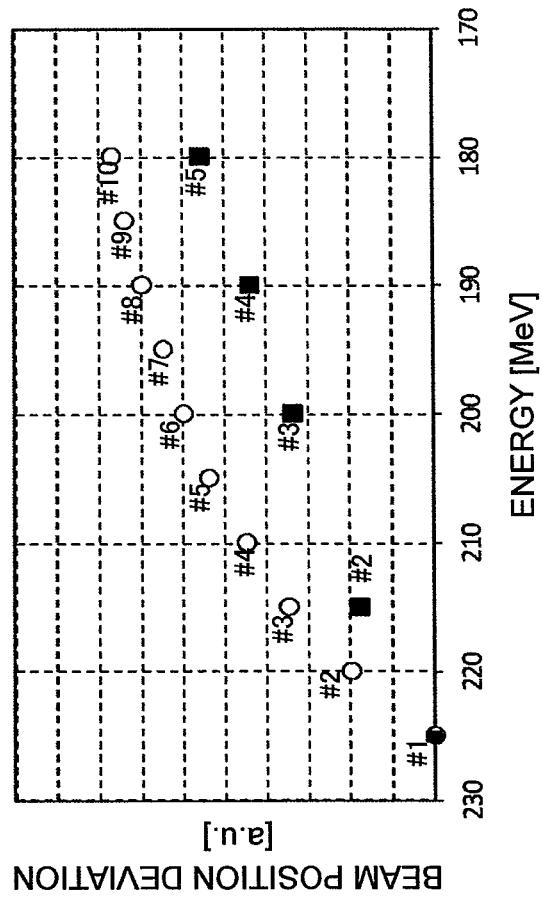
FIG. 7 is a graph showing beam position deviation at the irradiation position caused by magnetic field hysteresis of transport system bending magnets when energy scan operation is performed.

FIG. 7 is a graph showing the beam position deviation at the irradiation position caused by the magnetic field hysteresis of the transport system bending magnets when the energy scan operation is performed. The graph with white circles was obtained by starting the energy scan operation at 225 MeV (irradiation start energy) and changing the energy level at intervals of 5 MeV. The graph with squares was obtained by starting the energy scan operation at 225 MeV (irradiation start energy) and changing the energy level at intervals of 15 MeV. Each number (#1, #2, etc.) represents the number of times of the energy scan. It can be seen that the beam position deviation changes depending on the number of times of the energy scan. In other words, even if the irradiation is performed at the same energy level, the beam position deviation varies depending on the number of times of the energy scan executed to reach the intended energy level.

Figure 8:
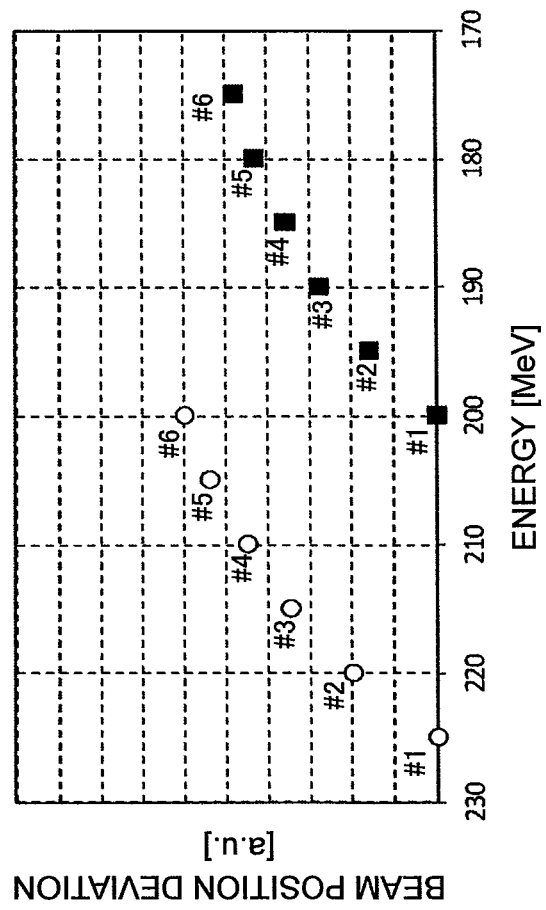
FIG. 8 is a graph showing the beam position deviation at the irradiation position in cases where the energy scan operation is performed in different energy ranges.

FIG. 8 is a graph showing the beam position deviation at the irradiation position in cases where the energy scan operation is performed in different energy ranges. Specifically, the beam energy was decreased six times in a 200-230 MeV range and in a 170-200 MeV range. It can be seen from the graph that the beam position deviation varies depending on the energy range of the energy scan operation even if the number of times of the energy scan is the same.

As above, the change in the magnetic field caused by the energy scan operation is determined by the target energy level and the number of steps of the energy scan executed to reach the energy level. Thus, the change in the magnetic field due to the hysteresis caused by the energy scan is compensated for by using a table describing a compensation value ratio for each energy scan step (number of times of changing the energy) as the current supply compensation value table 1 and a table describing the reference value of the compensation (basic compensation value) corresponding to each energy level as the current supply compensation value table 2. By compensating for the change in the magnetic field as described above, it becomes possible to omit the initialization operation of the transport system magnets. Therefore, even when the irradiation is performed by changing the energy level of the extracted ion beam, the time necessary for the switching of the energy level is shortened. Consequently, the treatment time can be reduced compared to the conventional technology. Incidentally, the current supply compensation value tables 2 and 3 are determined during the beam commissioning by conducting a learning process by actually using the ion beam.

The excitation current compensation according to this embodiment is effective when the energy level is changed in one direction (increased or decreased). In other words, the excitation current compensation of this embodiment is effective in irradiation operation in which the energy of the extracted ion beam is increased stepwise or decreased stepwise after the synchrotron has performed the initialization operation. Incidentally, "changing the energy of the extracted ion beam stepwise" can mean not only the method changing the energy at fixed intervals but also other methods changing the energy by desired increments/decrements depending on the irradiation conditions as will be explained later.

Next, the excitation current value compensation in this embodiment will be explained concretely. The following explanation will be given about the excitation current value of the bending magnet 20A of the beam transport system (gantry beam transport system 3) in a case where the energy scan operation is performed by decreasing stepwise the energy of the extracted ion beam in four steps of 220 MeV, 215 MeV, 210 MeV and 200 MeV.

First, the magnet excitation current for the first energy level of 220 MeV will be explained. According to the magnet current supply control table 1, the reference magnet excitation current value for the bending magnet 20A for the energy level 220 MeV equals 410 A. Since it is the first step of the energy scan operation, the compensation value ratio equals 0% according to the current supply compensation value table 1. While the basic compensation value for the magnet excitation current value for the energy level 220 MeV equals −2.4 A according to the current supply compensation value table 2, the compensation value equals 0 A since the compensation value ratio is 0%. Thus, the excitation current value is determined as 410 A+0 A=410 A.

Next, the magnet excitation current for the second step (215 MeV) of the energy scan will be explained. The reference excitation current value for the energy level 215 MeV equals 405 A according to the current supply control table 1. Since it is the second step of the energy scan operation, the current supply compensation value ratio equals 10% according to the current supply compensation value table 1. Since the basic compensation value for the energy level 215 MeV is −2.0 A according to the current supply compensation value table 2, the compensation value equals −0.2 A. Thus, the excitation current value is determined as 405 A−0.2 A=404.8 A.

Next, the magnet excitation current for the third step (210 MeV) of the energy scan will be explained. The reference excitation current value for the energy level 210 MeV equals 400 A according to the current supply control table 1. Since it is the third step of the energy scan operation, the current supply compensation value ratio equals 20% according to the current supply compensation value table 1. Since the basic compensation value for the energy level 210 MeV is −2.0 A according to the current supply compensation value table 2, the compensation value equals −0.4 A. Thus, the excitation current value is determined as 400 A−0.4 A=399.6 A.

Finally, the magnet excitation current for the fourth step (200 MeV) of the energy scan will be explained. The reference excitation current value for the energy level 200 MeV equals 390 A according to the current supply control table 1. Since it is the fourth step of the energy scan operation, the current supply compensation value ratio equals 30% according to the current supply compensation value table 1. Since the basic compensation value for the energy level 200 MeV is −1.5 A according to the current supply compensation value table 2, the compensation value equals −0.45 A. Thus, the excitation current value is determined as 390 A−0.45 A=389.55 A. In this case, the value in the fourth row of the current supply compensation value table 1 is referred to (since it is the fourth step in terms of the number of steps of the energy scan) even though 200 MeV is the fifth energy level counted from the start (220 MeV) in terms of the energy level.

As above, the excitation current value to be set for each magnet is calculated by using the current supply control table 1 as the reference for the excitation current value and the two current supply compensation value tables 2 and 3 specifying the compensation current value (compensation value).

In general, the excitation current value of each magnet used for deflecting the beam increases/decreases with the increase/decrease in the energy of the beam to be deflected. Therefore, according to this embodiment, when the accelerator is operated to increase stepwise or decrease stepwise the energy of the extracted ion beam, the excitation current values of magnets related to the deflection of the beam can also be increased or decreased stepwise and their initialization operation can be omitted as explained above. Consequently, the increase in the treatment time due to the initialization operation of the magnets can be reduced.

Also for the other bending magnets 15, 20B and 20C of the transport systems, the excitation current values are calculated by using current supply control tables 1 and current supply compensation value tables 2 and 3 prepared similarly for these magnets. As a comparative example of this embodiment, it is possible to previously calculate the compensation values for the excitation currents supplied to the transport system magnets for every combination of the extracted energy (energy of the extracted ion beam) and the number of times of changing the energy and prestore the precalculated compensation values in a memory. However, in order to store all the current value data, the memory is required to store approximately $2^N$ values (N: the number of energy levels). In the carbon beam therapy, for example, a memory capable of storing $2^{300}$ values (i.e., $10^{90}$ values) has to be prepared for the total number (300) of energy levels and thus the load on the system becomes extremely heavy. In contrast, the control in this embodiment calculating the compensation values from three data tables is capable of reducing the amount of data stored in the memory and lessening the load on the system.

Among the control command data (for the bending magnet 20A and the other magnets) calculated and generated as above, the control command data for the first energy level are outputted to the accelerator controller 52 and the transport system controller 53, while the remaining control command data are temporarily stored in a memory of the central control unit 50.

After the beam irradiation is started and the irradiation of the deepest layer (beam scan in the lateral directions) is finished, the setting patterns for the accelerator controller 52, the transport system controller 53 and the nozzle controller 51 are switched for the beam irradiation at the next energy level. The central control unit 50 reads out the data for the next energy level from its memory, outputs the data to the accelerator controller 52 and the transport system controller 53, and starts the irradiation for the next depth one step shallower than the deepest part (in the direction toward the body surface). In the above example, 404.8 A as the set value for the second energy level is set to the bending magnet 20A of the transport system.

By repeatedly performing such operation, each of the excitation current values for the bending magnets 15, 20A, 20B and 20C arranged along the beam path in the transport systems is set to change in a shape like upward stairs or downward stairs. Further, the bending magnets 15, 20A, 20B and 20C arranged along the beam path in the transport systems can be controlled according to settings capable of compensating for the deviation (change) in the magnetic field (caused by the energy scan operation) at every energy level.

Furthermore, such operation makes it possible to perform the beam irradiation while maintaining positional accuracy required for the energy scan operation necessary for the scanning irradiation method. Moreover, since low-priced DC power supplies are used as the power supplies for the bending magnets 15, 20A, 20B and 20C and appropriate excitation current values are set for these magnets without the need of executing the pattern operation, treatment irradiation control with high accuracy of the beam irradiation position becomes possible without causing an increase in the treatment time or the power supply cost.

Incidentally, the same operation method can be employed also for an irradiation method successively changing the energy level in the synchrotron operation cycle (i.e., extracting the beam at multiple energy levels by increasing or decreasing the energy level stepwise during one operation cycle of the synchrotron including acceleration, extraction and deceleration). Also in this case, beam control realizing high beam irradiation position accuracy and reducing the increase in the treatment time becomes possible. While the present invention has been applied to the bending magnets 15, 20A, 20B and 20C arranged along the beam path in the transport systems in the above embodiment, it is also possible to carry out the magnet control by applying an equivalent idea to the synchrotron magnets or to magnets of the transport systems other than the bending magnets.

What is claimed is:
1. A particle therapy system comprising:
   an accelerator that accelerates an ion beam to a preset energy level;
   an irradiation device that irradiates an irradiation target with the accelerated ion beam;
   a beam transport system that transports the ion beam extracted from the accelerator to the irradiation device; and
   an irradiation control apparatus that controls, in a period in which the accelerator performs an energy scan operation of successively changing by increasing or decreasing stepwise the energy level of the extracted ion beam, the excitation current value of a magnet installed in the accelerator or the beam transport system so as to increase or decrease stepwise the excitation current value based on the energy level of the extracted ion beam and the number of times of stepwise changing of the energy level to reach the intended energy level of the extracted ion beam.

2. The particle therapy system according to claim 1, wherein the irradiation control apparatus calculates, based on a compensation value ratio for each energy scan step corresponding to the number of times of the stepwise changing of the energy level and a reference magnet excitation current value and a basic compensation value of the magnet corresponding to the energy level of the ion beam, a compensation value for the reference magnet excitation current value and then calculates the excitation current value of the magnet.

3. The particle therapy system according to claim 2, wherein:
   the irradiation control apparatus includes a first data table in which the reference magnet excitation current values have been recorded, a second data table in which the compensation value ratio have been recorded, and a third data table in which the basic compensation values have been recorded, and
   the irradiation control apparatus acquires the reference magnet excitation current value of the magnet from the first data table, calculates the compensation value for the reference magnet excitation current value based on the second and third data tables, and then calculates the excitation current value of the magnet from the reference magnet excitation current value and the compensation value.

4. The particle therapy system according to claim 1, wherein the energy level is increased or decreased stepwise at fixed intervals.

* * * * *